(12) United States Patent
Cornes et al.

(10) Patent No.: US 6,376,424 B1
(45) Date of Patent: Apr. 23, 2002

(54) HERBICIDAL COMPOSITION

(75) Inventors: Derek Cornes, Allschwil; Jutta Glock, Mumpf, both of (CH)

(73) Assignee: Syngenta Crop Protection, Inc., Greensboro, NC (US)

( * ) Notice: Subject to any disclaimer, the term of this patent is extended or adjusted under 35 U.S.C. 154(b) by 0 days.

(21) Appl. No.: 09/611,340

(22) Filed: Jul. 6, 2000

Related U.S. Application Data

(63) Continuation-in-part of application No. 09/235,348, filed on Jan. 21, 1999, now Pat. No. 6,162,762.

(30) Foreign Application Priority Data

Jan. 21, 1998 (CH) .................................. 135/98

(51) Int. Cl.[7] ...................... A01N 25/32; A01N 43/653
(52) U.S. Cl. ...................................... 504/105; 504/110
(58) Field of Search .................................. 504/105, 110

(56) References Cited

U.S. PATENT DOCUMENTS

| | | | |
|---|---|---|---|
| 4,902,340 A | 2/1990 | Hubele | 71/94 |
| 5,006,656 A | 4/1991 | Shankar et al. | 544/263 |
| 5,041,157 A | 8/1991 | Seiler et al. | 71/92 |
| 5,114,462 A | 5/1992 | Moser et al. | 71/88 |
| 5,380,852 A | 1/1995 | Schutze et al. | 546/174 |
| 5,441,922 A | 8/1995 | Ort et al. | 504/104 |
| 5,516,750 A | 5/1996 | Willms et al. | 504/106 |
| 5,534,486 A | 7/1996 | Muller et al. | 504/273 |
| 5,541,148 A | 7/1996 | Glock et al. | 504/112 |
| 5,541,337 A | 7/1996 | Muller et al. | |

FOREIGN PATENT DOCUMENTS

| | | |
|---|---|---|
| DE | 43 31 448 | 3/1995 |
| DE | 196 12 943 | 10/1996 |
| EP | 0 094 349 | 11/1983 |
| EP | 0 174 562 | 3/1986 |
| EP | 0 375 061 | 12/1989 |
| EP | 0 492 366 | 7/1992 |
| EP | 507 171 | 10/1992 |
| EP | 0507 171 | 10/1992 |
| EP | 0 551 650 | 7/1993 |
| EP | 0 268 554 | 5/1998 |
| WO | 91/07874 | 6/1991 |
| WO | 94/00987 | 1/1994 |
| WO | 96/29870 | 10/1996 |
| WO | 97/18712 | 5/1997 |
| WO | WO 97/18712 | 5/1997 |
| WO | 98/13361 | 4/1998 |

OTHER PUBLICATIONS

Derwent Abstract 96–456603/46 corresponding to DE 19612943—A 1996.
Devine, et al; Physiology of Herbicide Action. Chapter 17.4: "Sofeners for Herbicides" pp. 376–387 1993.

Search Report in EP99100891.3–2110 Corresponding to US Ser. No. 09/235,348 (3 pages).

*Primary Examiner*—S. Mark Clardy
(74) *Attorney, Agent, or Firm*—William A. Teoli, Jr.

(57) ABSTRACT

A selective herbicidal composition for controlling grasses and weeds in crops of cultivated plants, comprising
a) a herbicidally effective amount of a herbicide of formula I

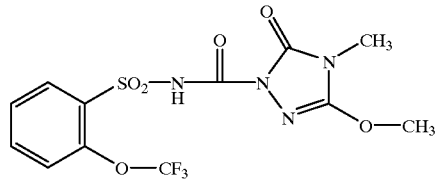

(I)

and
b) to antagonize the herbicide, an antidotally effective amount of a safener of formula 1.02

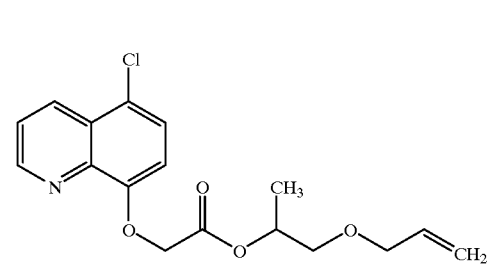

(1.02)

or of formula IIq (isoxadifen)

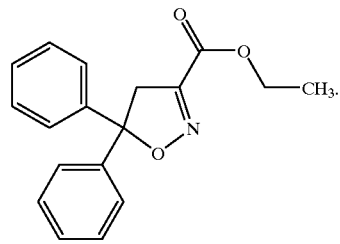

(IIq)

4 Claims, No Drawings

HERBICIDAL COMPOSITION

The present application is a Continuation-in-Part of application Ser. No. 09/235,348, filed Jan. 21, 1999, now U.S. Pat. No. 6,162,762.

The present invention relates to new selectively herbicidal compositions to combat grasses and weeds in crops of cultivated plants, especially in crops of cereals and rice which comprise a herbicide and a safener (antidote) and which protect the cultivated plants but not the weeds against the phytotoxic effect of the herbicide, and to the use of this composition for weed control in crops of cultivated plants.

When applying herbicides, the cultivated plants may also suffer severe damage owing to factors that include the concentration of the herbicide and the mode of application, the cultivated plant itself, the nature of the soil, and the climatic conditions such as exposure to light, temperature and rainfall.

To counteract this problem and similar ones, the proposal has already been made to use different compounds as safeners which are able to antagonise the harmful action of the herbicide on the cultivated plant, i.e. to protect the cultivated plant while leaving the herbicidal action on the weeds to be controlled virtually unimpaired. It has, however, been found that the proposed safeners often have a very specific action with respect not only to the cultivated plants but also to the herbicide, and in some cases also subject to the mode of application, i.e. a specific safener will often be suitable only for a specific cultivated plant and a specific class of herbicide or a specific herbicide. Compounds are known for example from WO 97/18712 which protect crop plants against the phytotoxic effect of specific herbicides. It has now been found that compounds of formula IIa

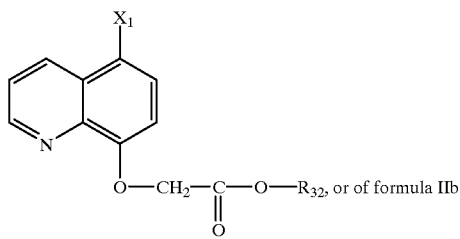
(IIa)

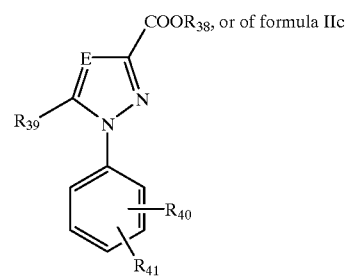
(IIb)

(IIc)

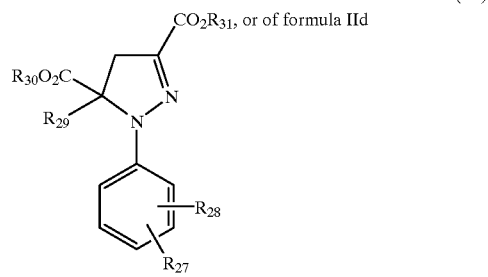
, or of formula IId (IId)

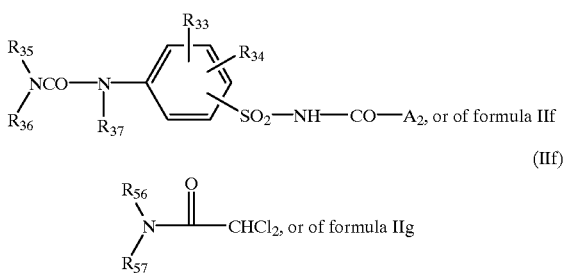
, or of formula IIf (IIf)

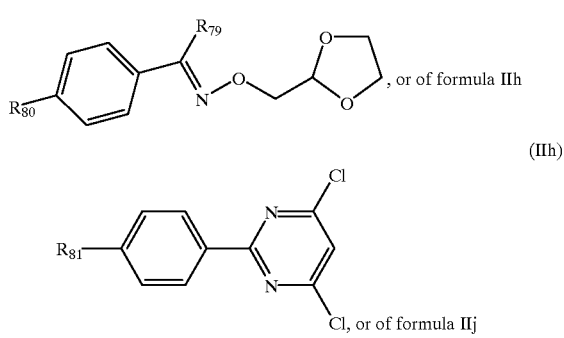

(IIg)

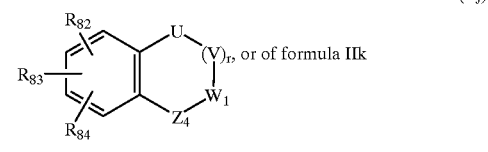
, or of formula IIh (IIh)

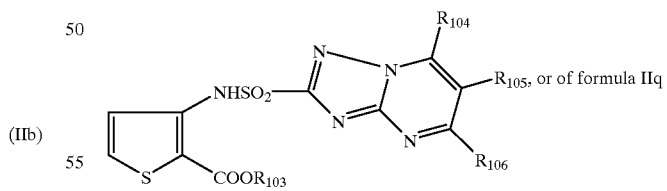
, or of formula IIj (IIj)

(IIk)

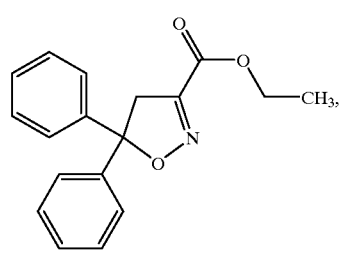

(IIq)

wherein the substituents are as defined hereinafter, are suitable for the protection of crop plants against the phytotoxic effect of a compound of formula I

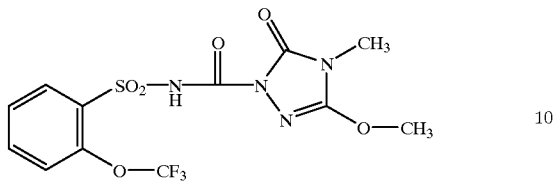

Accordingly, the invention provides a selective herbicidal composition comprising, in addition to customary inert formulation assistants such as carriers, solvents and wetting agents, a mixture of a) a herbicidally effective amount of a herbicide of formula I

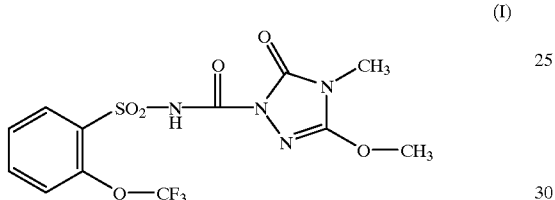

and b) to antagonise the herbicide, an antidotally effective amount of a safener of formula IIa

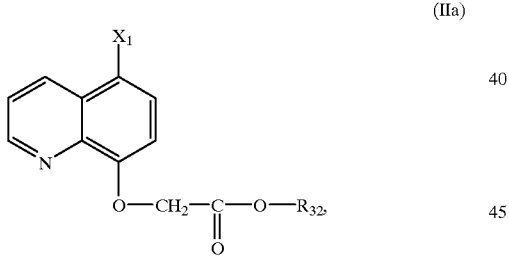

wherein
$R_{32}$ is hydrogen, $C_1$–$C_8$alkyl or $C_1$–$C_8$alkyl substituted by $C_1$–$C_6$alkoxy or $C_3$–$C_6$alkenyloxy and
$X_1$ is hydrogen or chlorine; or of formula IIb

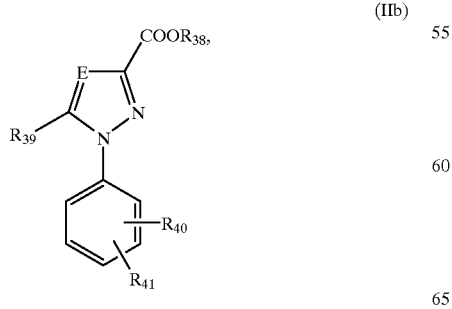

wherein E is nitrogen or methine;

$R_{38}$ is $C_1$–$C_4$alkyl;
$R_{39}$ is —$CCl_3$, phenyl or phenyl substituted by halogen, and
$R_{40}$ and $R_{41}$ independently of one another are hydrogen or halogen;
or of formula IIc

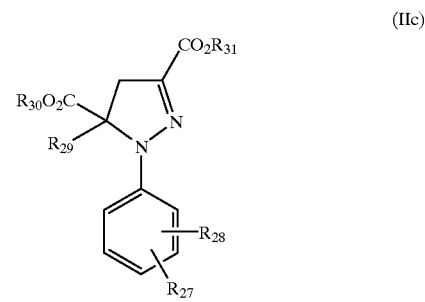

wherein $R_{27}$ and $R_{28}$ independently of one another are hydrogen or halogen, and
$R_{29}$, $R_{30}$ and $R_{31}$ independently of one another are $C_1$–$C_4$alkyl; or of formula IId

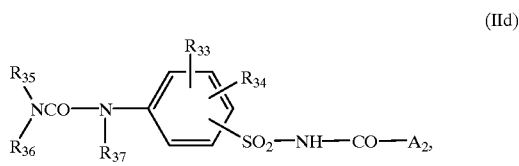

wherein $A_2$ is a

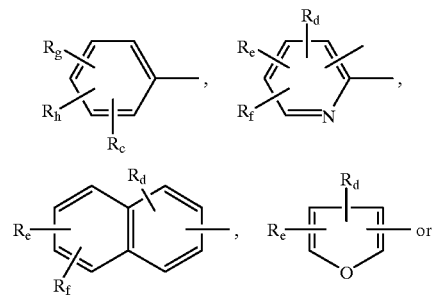

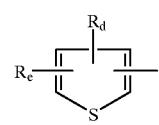

group, $R_{35}$ and $R_{36}$ independently of one another are hydrogen, $C_1$–$C_8$alkyl, $C_3$–$C_8$cycloalkyl, $C_3$–$C_6$alkenyl, $C_3$–$C_6$alkinyl,

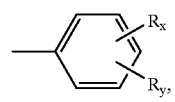

or C$_1$–C$_4$alkyl substituted by C$_1$–C$_4$alkoxy or

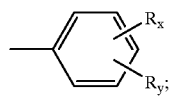

or R$_{35}$ and R$_{36}$ together form a C$_4$–C$_6$alkylene bridge, which may be broken by oxygen, sulfur, SO, SO$_2$, NH or —N(C$_1$–C$_4$alkyl)-; R$_{37}$ is hydrogen or C$_1$–C$_4$alkyl;

R$_{33}$ is hydrogen, halogen, cyano, trifluoromethyl, nitro, C$_1$–C$_4$alkyl, C$_1$–C$_4$alkoxy, C$_1$–C$_4$alkylthio, C$_1$–C$_4$alkylsulfinyl, C$_1$–C$_4$alkylsulfonyl, —COORj, —CONR$_k$R$_m$, —COR$_n$, —SO$_2$NR$_k$R$_m$ or —OSO$_2$—C$_1$–C$_4$alkyl;

R$_g$ is hydrogen, halogen, cyano, nitro, C$_1$–C$_4$alkyl, C$_1$–C$_4$halogenalkyl, C$_1$–C$_4$alkylthio, C$_1$–C$_4$alkylsulfinyl, C$_1$–C$_4$alkylsulfonyl, —COORj, —CONR$_k$R$_m$, —COR$_n$, —SO$_2$NR$_k$R$_m$—OSO$_2$—C$_1$–C$_4$alkyl, C$_1$–C$_6$alkoxy, or C$_1$–C$_6$alkoxy substituted by C$_1$–C$_4$alkoxy or halogen, C$_3$–C$_6$alkenyloxy, or C$_3$–C$_6$alkenyloxy substituted by halogen, or C$_3$–C$_6$alkinyloxy, or R$_{33}$ and R$_{34}$ together form a C$_3$–C$_4$alkylene bridge, which may be substituted by halogen or C$_1$–C$_4$alkyl, or they form a C$_3$–C$_4$alkenylene bridge, which may be substituted by halogen or C$_1$–C$_4$alkyl, or they form a C$_4$alkadienylene bridge, which may be substituted by halogen or C$_1$–C$_4$alkyl;

R$_{34}$ and R$_h$ independently of one another are hydrogen, halogen, C$_1$–C$_4$alkyl, trifluoromethyl, C$_1$–C$_6$alkoxy, C$_1$–C$_6$alkylthio or —COORj;

R$_c$ is hydrogen, halogen, nitro, C$_1$–C$_4$alkyl or methoxy;

R$_d$ is hydrogen, halogen, nitro, C$_1$–C$_4$alkyl, C$_1$–C$_4$alkoxy, C$_1$–C$_4$alkylthio, C$_1$–C$_4$alkylsulfinyl, C$_1$–C$_4$alkylsulfonyl, —COR$_j$ or CONR$_k$R$_m$;

R$_e$ is hydrogen, halogen, C$_1$–C$_4$alkyl, —COOR$_j$, trifluoromethyl or methoxy, or R$_d$ and R$_e$ together form a C$_3$–C$_4$alkylene bridge;

R$_f$ is hydrogen, halogen or C$_1$–C$_4$alkyl;

R$_x$ and R$_y$ independently of one another are hydrogen, halogen, C$_1$–C$_4$alkyl, C$_1$–C$_4$alkoxy, C$_1$–C$_4$alkylthio, —COOR$_{38}$, trifluoromethyl, nitro or cyano;

R$_j$, R$_k$ and R$_m$ independently of one another are hydrogen or C$_1$–C$_4$alkyl; or R$_k$ and R$_m$ together form a C$_4$–C$_6$alkylene bridge, which may be broken by oxygen, NH or —N(C$_1$–C$_4$alkyl)—;

R$_n$ is C$_1$–C$_4$alkyl, phenyl, or phenyl substituted by halogen, C$_1$–C$_4$alkyl, methoxy, nitro or trifluoromethyl;

R$_{38}$ is hydrogen, C$_1$–C$_{10}$alkyl, C$_1$–C$_4$alkoxy-C$_1$–C$_4$alkyl, C$_1$–C$_4$alkylthio-C$_1$–C$_4$alkyl, di-C$_1$–C$_4$alkylamino-C$_1$–C$_4$alkyl, halogen-C$_1$–C$_8$alkyl, C$_2$–C$_8$alkenyl, halogen-C$_2$–C$_8$alkenyl, C$_3$–C$_8$alkinyl, C$_3$–C$_7$cycloalkyl, halogen-C$_3$–C$_7$cycloalkyl, C$_1$–C$_8$alkylcarbonyl, allylcarbonyl, C$_3$–C$_7$cycloalkylcarbonyl, benzoyl which is unsubstituted or substituted on the phenyl ring up to three times identically or differently by halogen, C$_1$–C$_4$alkyl, halogen-C$_1$–C$_4$alkyl, halogen-C$_1$–C$_4$alkoxy or C$_1$–C$_4$alkoxy; or furoyl, thienyl; or C$_1$–C$_4$alkyl substituted by phenyl, halogenphenyl, C$_1$–C$_4$alkylphenyl, C$_1$–C$_4$alkoxyphenyl, halogen-C$_1$–C$_4$alkylphenyl, halogen-C$_1$–C$_4$alkoxyphenyl, C$_1$–C$_6$alkoxycarbonyl, C$_1$–C$_4$alkoxy-C$_1$–C$_8$alkoxycarbonyl, C$_3$–C$_8$alkenyloxycarbonyl, C$_3$–C$_8$alkinyloxycarbonyl, C$_1$–C$_8$alkylthiocarbonyl, C$_3$–C$_8$alkenylthiocarbonyl, C$_3$–C$_8$alkinylthiocarbonyl, carbamoyl, mono-C$_1$–C$_4$alkylaminocarbonyl, di-C$_1$–C$_4$alkylaminocarbonyl; or phenylaminocarbonyl, which is unsubstituted or substituted on the phenyl ring up to three times identically or differently by halogen, C$_1$–C$_4$alkyl, halogen-C$_1$–C$_4$alkyl, halogen-C$_1$–C$_4$alkoxy or C$_1$–C$_4$alkoxy, or once by cyano or nitro, or dioxolan-2-yl which is unsubstituted or substituted by one or two C$_1$–C$_4$alkyl radicals, or dioxan-2-yl, which is unsubstituted or substituted by one or two C$_1$–C$_4$alkyl radicals, or C$_1$–C$_4$alkl which is substituted by cyano, nitro, carboxyl or C$_1$–C$_8$alkylthio-C$_1$–C$_8$alkoxycarbonyl; or a compound of formula IIf

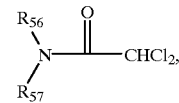

(IIf)

wherein R$_{56}$ and R$_{57}$ independently of one another are C$_1$–C$_6$alkyl or C$_2$–C$_6$alkenyl; or R$_{56}$ and R$_{57}$ together are

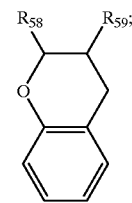

R$_{58}$ and R$_{59}$ independently of one another are hydrogen or C$_1$–C$_6$alkyl; or R$_{56}$ and R$_{57}$ together are

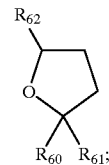

R$_{60}$ and R$_{61}$ independently of one another are C$_1$–C$_4$alkyl, or R$_{46}$ and R$_{47}$ together are —(CH$_2$)$_6$—;

$R_{62}$ is hydrogen, $C_1$–$C_4$alkyl or

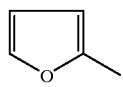

or $R_{56}$ and $R_{57}$ together are

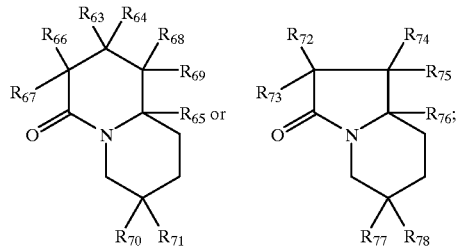

$R_{63}$, $R_{64}$, $R_{65}$, $R_{66}$, $R_{67}$, $R_{68}$, $R_{69}$, $R_{70}$, $R_{71}$, $R_{72}$, $R_{73}$, $R_{74}$, $R_{75}$, $R_{76}$, $R_{77}$, and $R_{78}$ independently of one another are hydrogen or $C_1$–$C_4$alkyl;

or a compound of formula IIg

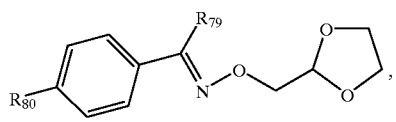

(IIg)

wherein $R_{79}$ is hydrogen or chlorine and $R_{80}$ is cyano or trifluoromethyl, or a compound of formula IIh

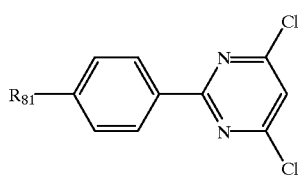

(IIh)

wherein $R_{81}$ is hydrogen or methyl, or of formula IIj

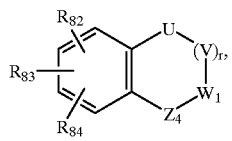

(IIj)

wherein $R_{82}$ is hydrogen, $C_1$–$C_4$alkyl, $C_1$–$C_4$alkyl substituted by $C_1$–$C_4$alkyl-$X_2$— or $C_1$–$C_4$halogenal-$X_2$—, $C_1$–$C_4$halogenalkyl, nitro, cyano, —COOR$_{85}$, —NR$_{86}$R$_{87}$, —SO$_2$NR$_{88}$R$_{89}$ or —CONR$_{90}$R$_{91}$;

$R_{83}$ is hydrogen, halogen, $C_1$–$C_4$alkyl, trifluoromethyl, $C_1$–$C_4$alkoxy or $C_1$–$C_4$halogenalkoxy;

$R_{84}$ is hydrogen, halogen or $C_1$–$C_4$alkyl;

U, V, $W_1$ and $Z_4$ independently of one another are oxygen, sulfur, C($R_{92}$)$R_{93}$, carbonyl, NR$_{94}$, a

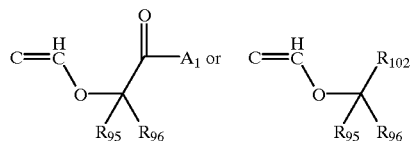

group, wherein $R_{102}$ is $C_2$–$C_4$alkenyl or $C_2$–$C_4$alkinyl; subject to the proviso that a) at least one of the ring members U, V, $W_1$ or $Z_4$ is carbonyl, and a ring member adjacent to this or these ring members is either the

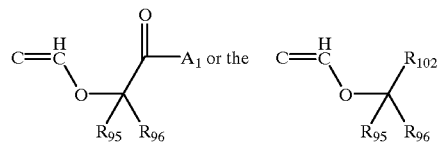

group, this group only occurring once; and b) two adjacent ring members U and V, V and $W_1$ and $W_1$ and $Z_4$ cannot simultaneously be oxygen;

$R_{95}$ and $R_{96}$ independently of one another are hydrogen or $C_1$–$C_8$alkyl; or $R_{95}$ and $R_{96}$ together form a $C_2$–$C_6$alkylene group;

$A_1$ is $R_{99}$-$Y_1$— or —NR$_{97}$R$_{98}$;

$X_2$ is oxygen or —S(O)$_s$;

$Y_1$ is oxygen or sulfur;

$R_{99}$ is hydrogen, $C_1$–$C_8$alkyl, $C_1$–$C_8$halogenalkyl, $C_1$–$C_4$alkoxy-$C_1$–$C_8$alkyl, $C_3$–$C_6$alkenyloxy-$C_1$–$C_8$-alkyl or phenyl-$C_1$–$C_8$-alkyl, wherein the phenyl ring may be substituted by halogen, $C_1$–$C_4$-a, trifluoromethyl, methoxy or methyl-S(O)$_s$—, $C_3$–$C_6$alkenyl, $C_3$–$C_6$halogenalkenyl, phenyl-$C_3$–$C_6$alkenyl, $C_3$–$C_6$alkinyl, p-$C_3$–$C_6$alkinyl, oxetanyl, furyl or tetrahydrofuryl;

$R_{85}$ is hydrogen or $C_1$–$C_4$alkyl;

$R_{86}$ is hydrogen, $C_1$–$C_4$alkyl or $C_1$–$C_4$alkylcarbonyl;

$R_{87}$ is hydrogen or $C_1$–$C_4$alkyl; or $R_{86}$ and $R_{87}$ together form a $C_4$ or $C_5$alkylene group;

$R_{88}$, $R_{89}$, $R_{90}$ and $R_{91}$ independently of one another are hydrogen or $C_1$–$C_4$alkyl; or $R_{88}$ and $R_{89}$ or $R_{90}$ and $R_{91}$ are independently of one another $C_4$ or $C_5$alkylene, in which a carbon atom may be substituted by oxygen or sulfur, or one or two carbon atoms by —NR$_{100}$—;

$R_{92}$ and $R_{100}$ independently of one another are hydrogen or $C_1$–$C_8$alkyl; or $R_{92}$ and $R_{93}$ together are $C_2$–$C_6$alkylene;

$R_{94}$ is hydrogen or $C_1$–$C_8$alkyl;

$R_{97}$ is hydrogen, $C_1$–$C_8$alkyl, phenyl, phenyl-$C_1$–$C_8$alkyl (in which the phenyl ring may be substituted by fluorine, chlorine, bromine, nitro, cyano, —OCH$_3$, $C_1$–$C_4$alkyl or CH$_3$SO$_2$—), $C_1$–$C_4$alkoxy-$C_1$–$C_8$alkyl, $C_3$–$C_6$alkenyl or $C_3$–$C_6$alkinyl;

$R_{98}$ is hydrogen, $C_1$–$C_8$alkyl, $C_3$–$C_6$alkenyl or $C_3$–$C_6$alkinyl; or $R_{97}$ and $R_{98}$ together are $C_4$ or $C_6$alkylene, in which a carbon atom may be substituted by oxygen or sulfur, or one or two carbon atoms by —NR$_{101}$—;

$R_{101}$ is hydrogen or $C_1$–$C_4$alkyl;
r is 0 or 1; and
s is 0, 1 or 2, or a compound of formula IIk

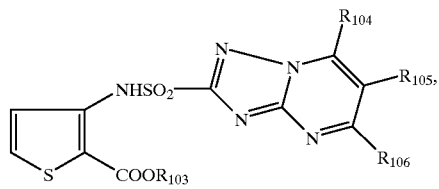

(IIk)

wherein $R_{103}$ is hydrogen, $C_1$–$C_6$alkyl, $C_3$–$C_6$cycloalkyl, $C_3$–$C_6$alkenyl or $C_3$–$C_6$alkinyl; and $R_{104}$, $R_{105}$ and $R_{106}$ are independently of one another hydrogen, $C_1$–$C_6$alkyl, $C_3$–$C_6$cycloalkyl or $C_1$–$C_6$alkoxy, subject to the proviso that one of the substituents $R_{104}$, $R_{105}$ or $R_{106}$ is different from hydrogen, or a compound of formula IIq

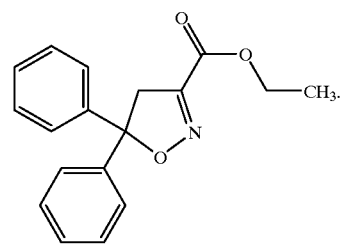

(IIq)

The alkyl groups occurring in the substituent definitions may be straight-chained or branched, and may for example be methyl, ethyl, propyl, butyl, pentyl, hexyl, heptyl or octyl, as well as their branched isomers. Alkoxy, alkylthio, alkoxycarbonyl, alkylcarbonyl, alkylsulfonyl, and alkylsulfinyl groups are derived from the said alkyl groups. Halogen is usually fluorine, chlorine, bromine or iodine, preferably fluorine, chlorine or bromine. In substituents such as —$NR_kR_m$, the alkyl radicals may be the same or different. In the preferred embodiment, they are the same. The term "substituted" may mean in the context of the present invention monosubstituted and, as far as possible, also polysubstituted.

The compound of formula 1 is described in EP-A-0 507 171. Compounds of formulae IIa, IIb, IIc, IId, IIf, IIg, IIh, IIj, and IIk are known from U.S. Pat. No. 5,041,157, U.S. Pat. No. 5,541,148, U.S. Pat. No. 5,006,656, EP-A-0 094 349, EP-A-0 551 650, EP-A-0 268 554, EP-A-0 375 061, EP-A-0 174 562, EP-A-492 366, WO 91/7874, WO 94/987, DE-A-19612943, WO 96/29870, WO 98/13361, and WO 97/18712. The compound of formula IIq is described in DE-A-4331448.

The compound of formula I may preferably be used according to the invention with the safeners of formulae IIa, IIb and IIc.

A very especially preferred composition according to the invention comprises the compound of formula I and the safener of formula IIa, wherein $X_1$ is chlorine and $R_{22}$ is —CH($CH_3$)$C_5H_{11}$—n.

Especially preferred compounds of the formulae and IIa toliq are listed in the following tables (formula IIe is the preferred compound of formula IId, and formulae IIm, IIn, IIo and IIp are the preferred compounds of formula IIh):

TABLE 1

Compounds of formula IIa: (IIa)

| Comp. no. | $X_1$ | $R_{32}$ |
|---|---|---|
| 1.01 | Cl | —CH($CH_3$)—$C_5H_{11}$-n |
| 1.02 | Cl | —CH($CH_3$)—$CH_2OCH_2CH$=$CH_2$ |
| 1.03 | Cl | H |
| 1.04 | Cl | $C_4H_9$-n |

TABLE 2

Compounds of formula IIb: (IIb)

| Comp. no. | $R_{38}$ | $R_{39}$ | $R_{40}$ | $R_{41}$ | E |
|---|---|---|---|---|---|
| 2.01 | $CH_3$ | Phenyl | 2-Cl | H | CH |
| 2.02 | $CH_3$ | Phenyl | 2-Cl | 4-Cl | CH |
| 2.03 | $CH_3$ | Phenyl | 2-F | H | CH |
| 2.04 | $CH_3$ | 2-Chlorophenyl | 2-F | H | CH |
| 2.05 | $C_2H_5$ | $CCl_3$ | 2-Cl | 4-Cl | N |
| 2.06 | $CH_3$ | Phenyl | 2-Cl | 4-$CF_3$ | N |
| 2.07 | $CH_3$ | Phenyl | 2-Cl | 4-$CF_3$ | N |
| 2.08 | $CH_3$ | 2-Fluorophenyl | 2-Cl | H | CH |

TABLE 3

Compounds of formula IIc (IIc)

| Comp. no. | $R_{29}$ | $R_{30}$ | $R_{31}$ | $R_{27}$ | $R_{28}$ |
|---|---|---|---|---|---|
| 3.01 | $CH_3$ | $CH_3$ | $CH_3$ | 2-Cl | 4-Cl |
| 3.02 | $CH_3$ | $C_2H_5$ | $CH_3$ | 2-Cl | 4-Cl |
| 3.03 | $CH_3$ | $C_2H_5$ | $C_2H_5$ | 2-Cl | 4-Cl |

TABLE 4

Compounds of formula IIe: (IIe)

A₂—C(O)—NHSO₂—[C₆H₄]—NH—C(O)—N(CH₃)(R₁₄)

| Comp. no. | A₂ | R₁₄ |
|---|---|---|
| 4.001 | 2-methoxyphenyl (OCH₃) | H |
| 4.002 | 2,4-dimethylphenyl | H |
| 4.003 | 1-methylnaphthyl | CH₃ |
| 4.004 | 2-methoxyphenyl (OCH₃) | CH₃ |

TABLE 5

Compounds of formula IIf: (IIf)

$R_{56}R_{57}N-C(O)-CHCl_2$

| Comp. no. | R₅₆ | R₅₇ | R₅₆ + R₅₇ |
|---|---|---|---|
| 5.001 | CH₂=CHCH₂ | CH₂=CHCH₂ | — |
| 5.002 | — | — | 2,2-dimethyl-tetrahydrofuran-based |
| 5.003 | — | — | 2,5-dimethyl-tetrahydrofuran-based |
| 5.004 | — | — | cyclohexyl-tetrahydrofuran-based |
| 5.005 | — | — | furan/tert-butoxy propyl group |
| 5.006 | — | — | 3-methylchroman |
| 5.007 | — | — | pyrrolidinone with gem-dimethyl and neopentyl substituents |

TABLE 6

Compounds of formula IIg: (IIg)

$R_{80}-[C_6H_4]-C(R_{79})=N-O-CH_2-[1,3\text{-dioxolan-2-yl}]$

| Comp. no. | R₈₀ | R₇₉ |
|---|---|---|
| 6.01 | H | CN |
| 6.02 | Cl | CF₃ |

TABLE 7

Compounds of formula IIh: (IIh)

[Structure: R₈₁-phenyl-pyrimidine with 4,6-dichloro substituents]

| Comp. no. | R₈₁ |
|---|---|
| 7.01 | H |
| 7.02 | CH$_3$ |

TABLE 8

Compounds of formula IIm (IIm)

[Structure: benzene ring fused with lactone bearing (V)$_r$ and Z$_4$, substituent R$_{82}$]

| Comp. no. | R$_{82}$ | Z$_4$ | V | r |
|---|---|---|---|---|
| 8.001 | H | C=CH–O–CH$_2$–CH(=CH$_2$) | O | 1 |
| 8.002 | H | C=CH–O–CH$_2$–COOCH$_3$ | O | 1 |
| 8.003 | H | C=CH–O–CH$_2$–C≡CH | O | 1 |
| 8.004 | H | C=CH–O–CH$_2$–COOCH(CH$_3$)(CH$_2$)$_4$CH$_3$ | O | 1 |
| 8.005 | H | C=CH–O–CH$_2$–COOCH$_3$ | CH$_2$ | 1 |
| 8.006 | H | C=CH–O–CH(CH$_3$)–COOCH$_3$ | CH$_2$ | 1 |
| 8.007 | H | C=CH–O–CH$_2$–COOCH$_3$ | S | 1 |
| 8.008 | H | C=CH–O–CH$_2$–C≡CH | S | 1 |
| 8.009 | H | C=CH–O–CH$_2$–C≡CH | NCH$_3$ | 1 |

TABLE 8-continued

Compounds of formula IIm (IIm)

| Comp. no. | R₈₂ | Z₄ | V | r |
|---|---|---|---|---|
| 8.010 | H | C=CH-O-CH₂-COOCH₃ | NCH₃ | 1 |
| 8.011 | H | C=CH-O-CH(CH₃)-COOCH₃ | NCH₃ | 1 |
| 8.012 | H | C=CH-O-CH(CH₃)-COOCH₃ | O | 1 |
| 8.013 | H | C=CH-O-CH(CH₃)-COOCH₃ | S | 1 |

TABLE 9

Compounds of formula IIn (IIn)

| Comp. no. | U | R₈₂ | Z₄ |
|---|---|---|---|
| 9.001 | O | H | C=CH-O-CH₂-COOCH₃ |
| 9.002 | O | H | C=CH-O-CH₂-C≡CH |
| 9.003 | O | 5-Cl | C=CH-O-CH₂-COOCH₃ |
| 9.004 | CH₂ | H | C=CH-O-CH₂-COOCH₃ |
| 9.005 | CH₂ | H | C=CH-O-CH₂-COO-CH₂-C₆H₅ |
| 9.006 | CH₂ | H | C=CH-O-CH₂-COOC₂H₅ |
| 9.007 | NH | 5-Cl | C=CH-O-CH(CH₃)-COOCH₃ |

TABLE 9-continued

Compounds of formula IIn (IIn)

| Comp. no. | U | $R_{82}$ | $Z_4$ |
|---|---|---|---|
| 9.008 | NH | 5-Cl | C=CH−O−CH$_2$−COOCH$_3$ |
| 9.009 | NH | H | C=CH−O−CH$_2$−COOCH$_3$ |
| 9.010 | NH | H | C=CH−O−CH(CH$_3$)−COOCH$_3$ |
| 9.011 | NCH$_3$ | H | C=CH−O−CH(CH$_3$)−COOCH$_3$ |
| 9.012 | NCH$_3$ | H | C=CH−O−CH$_2$−COOCH$_3$ |

TABLE 10

Compounds of formula IIo (IIo)

| Comp. no. | U | V | r | $W_1$ | $Z_4$ | $R_{82}$ |
|---|---|---|---|---|---|---|
| 10.001 | O | C=O | 1 | C=CH−O−CH$_2$−C≡CH | CH$_2$ | H |
| 10.002 | O | C=O | 1 | C=CH−O−CH$_2$−COOCH$_3$ | CH$_2$ | H |
| 10.003 | CH$_2$ | C=O | 1 | C=CH−O−CH(CH$_3$)−COOCH$_3$ | CH$_2$ | H |
| 10.004 | CH$_2$ | C=O | 1 | C=CH−O−CH$_2$−COOCH$_3$ | CH$_2$ | H |
| 10.005 | CH$_2$ | CH$_2$ | 1 | C=CH−O−CH$_2$−COOCH$_3$ | C=O | H |
| 10.006 | CH$_2$ | CH$_2$ | 1 | C=CH−O−CH(CH$_3$)−COOCH$_3$ | C=O | H |

TABLE 10-continued

Compounds of formula IIo (IIo)

| Comp. no. | U | V | r | W$_1$ | Z$_4$ | R$_{82}$ |
|---|---|---|---|---|---|---|
| 10.007 | NCH$_3$ | C=O | 1 | C=CH-O-CH$_2$-COOCH$_3$ | CH$_2$ | H |

TABLE 11

Compounds of formula IIp (IIp)

| Comp. no. | R$_{82}$ | W$_1$ |
|---|---|---|
| 11.001 | 6-Cl | C=CH-O-CH$_2$-COOCH$_3$ |
| 11.002 | 6-Cl | C=CH-O-CH(CH$_3$)-COOCH$_3$ |
| 11.003 | H | C=CH-O-CH$_2$-C≡CH |
| 11.004 | H | C=CH-O-CH(CH$_3$)-COOCH$_3$ |
| 11.005 | H | C=CH-O-CH$_2$-COOCH$_3$ |

TABLE 12

Compounds of formula IIk (IIk)

| Comp no. | R$_{103}$ | R$_{104}$ | R$_{105}$ | R$_{106}$ |
|---|---|---|---|---|
| 12.01 | CH$_3$ | H | Cyclopropyl | H |
| 12.02 | CH$_3$ | C$_2$H$_5$ | Cyclopropyl | H |
| 12.03 | CH$_3$ | Cyclopropyl | C$_2$H$_5$ | H |
| 12.04 | CH$_3$ | CH$_3$ | H | H |
| 12.05 | CH$_3$ | CH$_3$ | Cyclopropyl | H |
| 12.06 | CH$_3$ | OCH$_3$ | OCH$_3$ | H |
| 12.07 | CH$_3$ | CH$_3$ | OCH$_3$ | H |
| 12.08 | CH$_3$ | OCH$_3$ | CH$_3$ | H |
| 12.09 | CH$_3$ | CH$_3$ | CH$_3$ | H |
| 12.10 | C$_2$H$_5$ | CH$_3$ | CH$_3$ | H |
| 12.11 | C$_2$H$_5$ | OCH$_3$ | OCH$_3$ | H |
| 12.12 | H | OCH$_3$ | OCH$_3$ | H |
| 12.13 | H | CH$_3$ | CH$_3$ | H |
| 12.14 | C$_2$H$_5$ | H | H | CH$_3$ |
| 12.15 | H | H | H | CH$_3$ |
| 12.16 | CH$_3$ | H | H | CH$_3$ |

The invention also relates to a method of selectively controlling weeds in crops of cultivated plants, which comprises treating said cultivated plants, the seeds or seedlings or the crop area thereof, concurrently or separately, with a herbicidally effective amount of the herbicide of formula I and, to antagonise the herbicide, an antidotally effective amount of the safener of formula IIa, IIb, IIc IId, IIf, IIg, IIh, IIj, IIk or IIq.

Crop plants which may be protected by the safeners of formula IIa, IIb, IIc IId, IIf, IIg, IIh, IIj, IIk or IIq from the damaging effect of the herbicides mentioned hereinbefore are in particular cereals and rice. Crops will also be understood as meaning those crops that have been made tolerant to herbicides or classes of herbicides by conventional breeding or genetic engineering methods.

The weeds to be controlled may be monocot as well as dicot weeds, typically Stellaria, Nasturtium, Agrostis, Digitaria, Avena, Setaria, Sinapis, Lolium, Solanum, Echinochloa, Scirpus, Monochoria, Sagittaria, Bromus, Alopecurus, Sorghum halepense, Rottboellia, Cyperus, Abutilon, Sida, Xanthium, Amaranthus, Chenopodium, Ipomoea, Chrysanthemum, Galium, Viola, and Veronica.

Crop areas will be understood as meaning the areas already under cultivation with the cultivated plants or seeds thereof, as well as the areas intended for cropping with said cultivated plants.

Depending on the end use, a safener of formula II can be used for pretreating seeds of the crop plants (dressing of seeds or seedlings) or it can be incorporated in the soil before or after sowing. It can, however, also be applied by itself alone or together with the herbicide postemergence. Treatment of the plant or the seeds with the safener can therefore in principle be carried out irrespective of the time of application of the herbicide. Treatment can, however, also be carried out by simultaneous application of the phytotoxic chemical and safener (e.g. as tank mixture). The concentration of safener with respect to the herbicide will depend substantially on the mode of application. Where a field treatment is carried out either by using a tank mixture with a combination of safener and herbicide or by separate application of safener and herbicide, the ratio of safener to herbicide will usually be from 1:100 to 1:1, and preferably 1:50 to 5:1.

In field treatment it is usual to apply 0.001 to 5.0 kg safener/ha, preferably 0.001 to 0.5 kg safener/ha.

The rate of application of herbicide is usually in the range from 0.001 to 2 kg/ha, but will preferably be from 0.005 to 1 kg/ha.

The compositions of this invention are suitable for all methods of application commonly used in agriculture, including preemergence application, postemergence application and seed dressing.

For seed dressing, 0.001 to 10 g of safener/kg of seeds, preferably 0.05 to 2 g of safener/kg of seeds, is usually applied. If the safener is used in liquid form shortly before sowing to effect soaking, then it is preferred to use safener solutions that contain the active ingredient in a concentration of 1 to 10000 ppm, preferably of 100 to 1000 ppm.

For application, it is expedient to process the safeners of formula II, or mixtures of the safeners of formula II and the herbicides of formula I, together with the customary assistants of formulation technology to formulations, typically to emulsifiable concentrates, coatable pastes, directly sprayable or dilutable solutions, dilute emulsions, wettable powders, soluble powders, dusts, granulates or microcapsules.

Such formulations are described, for example, in WO 97/34485 on pages 9 to 13. The formulations are prepared in known manner, for example by homogeneously mixing or grinding the active ingredients with liquid or solid formulation assistants, typically solvents or solid carriers. Surface-active compounds (surfactants) may additionally be used for preparing the formulations. Suitable solvents and solid carriers for this purpose are described in WO 97/34485 on page 6.

Depending on the herbicide of formula I to be formulated, suitable surface-active compounds are nonionic, cationic and/or anionic surfactants and surfactant mixtures having good emulsifying, dispersing and wetting properties. Examples of suitable anionic, nonionic, and cationic surfactants are listed in WO 97/34485 on pages 7 and 8. Also the surfactants customarily employed in the art of formulation and described, inter alla, in "Mc Cutcheon's Detergents and Emulsifiers Annual" MC Publishing Corp., Ridgewood N.J., 1981, Stache, H., "Tensid-Taschenbuch" (Handbook of Surfactants), Carl Hanser Verlag, MunichNienna, 1981, and M. and J. Ash, "Encyclopedia of Surfactants", Vol I–III, Chemical Publishing Co., New York, 1980–81 are suitable for manufacture of the herbicides according to the invention.

The herbicidal compositions will usually contain from 0.1 to 99% by weight, preferably from 0.1 to 95% by weight, of compound mixture of the compound of formula I and the compounds of formula IIa, IIb, IIc IId, IIf, IIg, IIh, IIj, IIk or IIq, from 1 to 99.9% by weight of a solid or liquid formulation assistant, and from 0 to 25% by weight, preferably from 0.1 to 25% by weight, of a surfactant.

Whereas it is customarily preferred to formulate commercial products as concentrates, the end user will normally use dilute formulations.

The compositions may also contain further ingredients, such as: stabilisers, e.g. where appropriate epoxidised vegetable oils (epoxidised coconut oil, rapeseed oil, or soybean oil); antifoams, typically silicone oil; preservatives; viscosity regulators; binders; and tackifiers; as well as fertilisers or other chemical agents. Different methods and techniques may suitably be used for applying the safeners of formula II or compositions containing them for protecting cultivated plants from the harmful effects of herbicides of formula I, conveniently the following:

i) Seed Dressing a) Dressing the seeds with a wettable powder formulation of the active ingredient of formula II by shaking in a vessel until the safener is uniformly distributed on the surface of the seeds (dry treatment). About 1 to 500 g of active ingredient of formula IIa, IIb, IIc IId, IIf, IIg, IIh, IIj, IIk or IIq (4 g to 2 kg of wettable powder) are used per 100 kg of seeds.

Dressing the seeds with an emulsifiable concentrate of the active ingredient of formula IIa, IIb, IIc IId, IIf, IIg, IIh, IIj, IIk or IIq according to method a) (wet treatment).

c) Dressing by immersing the seeds in a mixture containing 100–1000 ppm of active ingredient of formula IIa, IIb, IIc IId, IIf, IIg, IIh, IIj, IIk or IIq for 1 to 72 hours and, where appropriate, subsequently drying them (seed soaking).

In keeping with the natural environment, the preferred method of application is either seed dressing or treatment of the germinated seedlings, because the safener treatment is fully concentrated on the target crop. Usually 1 to 1000 g, preferably 5 to 250 g, of safener is used per 100 kg of seeds. However, depending on the method employed, which also permits the use of other chemical agents or micronutrients, the concentrations may deviate above or below the indicated limit values (repeat dressing).

ii) Application as a Tank Mixture

A liquid formulation of a mixture of safener and herbicide (reciprocal ratio from 10:1 to 1:100) is used, the concentration of herbicide being from 0.005 to 5.0 kg/ha. This tank mixture is applied before or after sowing.

iii) Application in the Furrow

The active ingredient of formula IIa, IIb, IIc IId, IIf, IIg, IIh, IIj, IIk or IIq formulated as emulsifiable concentrate, wettable powder or granulate is applied to the open furrow in which the seeds have been sown. After covering the furrow, the herbicide is applied pre-emergence in conventional manner.

iv) Controlled Release of Compound

The compound of formula Formel IIa, IIb, IIc IId, IIf, IIg, IIh, IIj, IIk or IIq is applied in solution to a mineral granular carrier or to polymerised granules (urea/formaldehyde) and then dried. A coating can then be applied (coated granules) that allows the herbicide to be released at a controlled rate over a specific period of time.

Particularly preferred formulations are made up as follows:

(%=per cent by weight)

Emulsifiable Concentrates:

Compound mixture: 1 to 90%, preferably 5 to 20%

Surfactant: 1 to 30%, preferably 10 to 20%

Liquid carrier: 5 to 94%, preferably 70 to 85%

Dusts:

Compound mixture: 0.1 to 10%, preferably 0,1 to 5%

Solid carrier: 99.9 to 90%, preferably 99,9 to 99%

Suspension Concentrates:

Compound mixture: 5 to 75%, preferably 10 to 50%

Water: 94 to 30%, preferably 88 to 20%

Surfactant: 1 to 30%, preferably 2 to 20%

Wettable Powders:

Compound mixture: 1 to 90%, preferably 10 to 80%

Surfactant: 1 to 30%, preferably 10 to 20%

Solid carrier: 5 to 95%, preferably 15 to 90%

Granulates:

Compound mixture: 0.1 to 30%, preferably 0,1 to 15%

Solid carrier: 99.5 to 70%, preferably 97 to 85%

The invention is illustrated by the following non-limitative Examples.

Formulation Examples for mixtures of herbicides of formula I and safeners of formula IIa, IIb, IIc IId, IIf, IIg, IIh, IIj, IIk or IIq (%=per cent by weight)

| F1. Emulsifiable concentrates | a) | b) | c) | d) |
|---|---|---|---|---|
| Compound mixture | 5% | 10% | 25% | 50% |
| Calcium dodecylbenzenesulfonate | 6% | 8% | 6% | 8% |
| Polyethoxylated castor oil (36 mol EO) | 4% | — | 4% | 4% |
| Octylphenol polyethoxylate (7—8 mol EO) | — | 4% | — | 2% |
| Cyclohexanone | — | — | 10% | 20% |
| Arom. hydrocarbon mixture $C_9$–$C_{12}$ | 85% | 78% | 55% | 16% | mixture $C_9$–$C_{12}$

Emulsions of any desired concentration can be prepared by diluting such concentrates with water.

| F2. Solutions | a) | b) | c) | d) | |
|---|---|---|---|---|---|
| Compound mixture | 5% | 10% | | 50% | 90% |
| 1-Methoxy-3-(3-methoxy-propoxy)-propane | — | 20% | 20% | — | |
| Polyethylene glycol MG 400 | 20% | 10% | — | — | |
| N-Methyl-2-pyrrolidone | — | — | | 30% | 10% |
| Arom. hydrocarbon mixture $C_9$–$C_{12}$ | 75% | 60% | — | — | |

The solutions are suitable for use in the form of microdrops.

| F3. Wettable powders | a) | b) | c) | d) |
|---|---|---|---|---|
| Compound mixture | 5% | 25% | 50% | 80% |
| Sodium ligninsulfonate | | 4% | — | 3% |
| Sodium lauryl sulfate | 2% | 3% | — | 4% |
| Sodium diisobutylnaphthalene | — | 6% | 5% | 6% |
| Octylphenol polyethoxylate (7–8 mol EO) | — | 1% | 2% | — |
| Highly dispersed silicic acid | 1% | 3% | 5% | 10% |
| Kaolin | 88% | 62% | 35% | — |

The compound is throughly mixed with the adjuvants and this mixture is ground in a suitable mill to give wettable powders which can be diluted with water to give suspensions of any desired concentration.

| F4. Coated granulates | a) | b) | c) |
|---|---|---|---|
| Compound mixture | 0.1% | 5% | 15% |
| Highly dispersed silicic acid | 0.9% | 2% | 2% |
| Inorganic substrate | 99.0% | 93% | 83% |

(AE 0.1–1 mm) such as $CaCO_3$ or $SiO_2$

The compound mixture is dissolved in dichloromethane, the solution is sprayed on to the carrier, and the solvent is removed under vacuum.

| F5. Coated granulates | a) | b) | c) |
|---|---|---|---|
| Compound mixture | 0.1% | 5% | 15% |
| Polyethylene glycol MG 200 | 1.0% | 2% | 3% |
| Highly dispersed silicic acid | 0.9% | 1% | 2% |
| Inorganic substrate | 98.0% | 92% | 80% |

(AE 0.1–1 mm) such as $CaCO_3$ or $SiO_2$

The finely ground active substance is uniformly applied in a mixer to the carrier moistened with polyethylene glycol. Non-dusty coated granulates are obtained in this manner.

| F6. Extruder granulates | a) | b) | c) | d) |
|---|---|---|---|---|
| Compound mixture | 0.1% | 3% | 5% | 15% |
| Sodium ligninsulfonate | 1.5% | 2% | 3% | 4% |
| Carboxymethylcellulose | 1.4% | 2% | 2% | 2% |
| Kaolin | 97.0% | 93% | 90% | 79% |

The compound is mixed and ground with the adjuvants, and the mixture is moistened with water. This mixture is extruded and then dried in a stream of air.

| F7. Dusts | a) | b) | c) |
|---|---|---|---|
| Compound mixture | 0.1% | 1% | 5% |
| Talc | 39.9% | 49% | 35% |
| Kaolin | 60.0% | 50% | 60% |

Ready for use dusts are obtained by mixing the active ingredient with the carriers on a suitable mill.

| F8. Suspension concentrates | a) | b) | c) | d) |
|---|---|---|---|---|
| Compound mixture | 3% | 10% | 25% | 50% |
| Ethylene glycol | 5% | 5% | 5% | 5% |
| Nonylphenol polyethoxylate (15 mol EO) | — | 1% | 2% | — |
| Sodium ligninsulfonate | 3% | 3% | 4% | 5% |
| Carboxymethylcellulose | 1% | 1% | 1% | 1% |
| 37% aqueous formaldehyde solution | 0.2% | 0.2% | 0.2% | 0.2% |
| Silicone oil emulsion | 0.8% | 0.8% | 0.8% | 0.8% |
| Water | 87% | 79% | 62% | 38% |

The finely ground active substance is intimately mixed with the adjuvants to give a suspension concentrate from which suspensions of any desired concentration can be prepared by dilution with water.

It is often expedient to formulate the compound of formula I and the components of formulae IIa to IIq individually and only to combine them shortly before application in the applicator in the desired mixture ratio as tank mixture in water.

The following Examples illustrate the ability of the safeners of formula IIa, IIb, IIc IId, IIf, IIg, IIh, IIj, IIk or IIq to protect cultivated plants from the phytotoxic action of herbicides of formula I.

BIOLOGICAL EXAMPLES

EXAMPLE B1

Post-emergent applications of mixtures of a herbicide of formula I with a safener of formulae IIa to IIq to cereals.

Under greenhouse conditions, wheat is grown in plastic pots to the 2.5-leaf stage. In this stage, both the herbicide of formula I alone and the mixture of the herbicide with a safener of formulae IIa to IIq are applied to the test plants. The test substances (Formulation Examples F3 a) and b)) are applied as aqueous suspension with 500 l water/ha. Ten days after the application, the results are evaluated on a percent scale. The results obtained show that, with the safeners of formulae IIa to IIq, the damage caused to wheat can be markedly reduced by the herbicide of formula I.

Examples of the selective effect of the compositions of the invention are given in Tables B1 to B4:

TABLE B1

| Plant: | Herbicide of formula 1:60 g/ha | Herbicide of formula 1:60 g/ha Safener no. 6.02: 15 g/ha |
|---|---|---|
| Wheat | 20 | 10 |
| Chenopodium | 90 | 80 |
| Emex | 90 | 90 |
| Raphanus | 80 | 80 |
| Setaria | 80 | 80 |

TABLE B2

| Plant: | Herbicide of formula 1:15 g/ha | Herbicide of formula 1:15 g/ha Safener no. 1,01: 4 g/ha |
|---|---|---|
| Wheat | 10 | 5 |
| Chenopodium | 90 | 90 |
| Emex | 80 | 90 |
| Raphanus | 80 | 80 |
| Setaria | 70 | 70 |

TABLE B3

| Plant: | Herbicide of formula 1:15 g/ha | Herbicide of formula 1:15 g/ha Safener no. 4.001: 4 g/ha |
|---|---|---|
| Wheat | 10 | 5 |
| Chenopodium | 80 | 80 |
| Emex | 80 | 90 |
| Raphanus | 80 | 80 |
| Setaria | 70 | 80 |

TABLE B4

| Plant: | Herbicide of formula 1:15 g/ha | Herbicide of formula 1:15 g/ha Safener no. 3,03: 4 g/ha |
|---|---|---|
| Wheat | 10 | 5 |
| Chenopodium | 90 | 90 |
| Emex | 80 | 90 |
| Raphanus | 80 | 80 |
| Setaria | 70 | 70 |

The same results are obtained by formulating a compound of formulae I and IIa to IIq in accordance with Examples F1, F2 and F4 to F7.

EXAMPLE B2

Post-emergent applications of mixtures of a herbicide of formula I with a safener of formulae IIa to IIq to barley.

Under greenhouse conditions, barley is grown in plastic pots to the 2.5-leaf stage. In this stage, both the herbicide of formula I alone and the mixture of the herbicide with a safener of formulae IIa to IIq are applied to the test plants. The test substances (Formulation Examples F3 a) and b)) are applied as aqueous suspension with 500 l water/ha. Ten days after the application, the results are evaluated on a percent scale. The results obtained show that, with the safeners of formulae IIa to IIq, the damage caused to barley can be markedly reduced by the herbicide of formula I.

Examples of the selective effect of the compositions of the invention are given in Tables B5 to B11:

TABLE B5

| Plant: | Herbicide of formula 1:60 g/ha | Herbicide of formula 1:60 g/ha Safener no. 3,03: 15 g/ha |
|---|---|---|
| Barley | 40 | 30 |
| Chenopodium | 90 | 80 |
| Emex | 90 | 90 |
| Raphanus | 80 | 80 |
| Setaria | 80 | 80 |

TABLE B6

| Plant: | Herbicide of formula 1:60 g/ha | Herbicide of formula 1:60 g/ha Safener no. 6.02: 15 g/ha |
|---|---|---|
| Barley | 40 | 30 |
| Chenopodium | 90 | 80 |
| Emex | 90 | 90 |
| Raphanus | 80 | 80 |
| Setaria | 80 | 80 |

TABLE B7

| Plant: | Herbicide of formula 1:60 g/ha | Herbicide of formula 1:60 g/ha Safener no. 4.001: 15 g/ha |
|---|---|---|
| Barley | 40 | 30 |
| Chenopodium | 90 | 80 |
| Emex | 90 | 90 |
| Raphanus | 80 | 80 |
| Setaria | 80 | 80 |

TABLE B8

| Plant: | Herbicide of formula 1:60 g/ha | Herbicide of formula 1:60 g/ha Safener no. 2,05: 15 g/ha |
|---|---|---|
| Barley | 40 | 30 |
| Chenopodium | 90 | 90 |
| Emex | 90 | 90 |
| Raphanus | 80 | 90 |
| Setaria | 80 | 80 |

TABLE B9

| Plant: | Herbicide of formula 1:60 g/ha | Herbicide of formula 1:60 g/ha Safener no. 2,01: 15 g/ha |
|---|---|---|
| Barley | 40 | 10 |
| Chenopodium | 90 | 90 |
| Emex | 90 | 90 |
| Raphanus | 80 | 80 |
| Setaria | 80 | 70 |

TABLE B10

| Plant: | Herbicide of formula 1:15 g/ha | Herbicide of formula 1:15 g/ha Safener no. 2,01: 4 g/ha |
|---|---|---|
| Barley | 30 | 0 |
| Chenopodium | 90 | 90 |
| Emex | 80 | 90 |
| Raphanus | 80 | 80 |
| Setaria | 70 | 70 |

TABLE B11

| Plant: | Herbicide of formula 1:60 g/ha | Herbicide of formula 1:60 g/ha Safener no. 5.006: 15 g/ha |
|---|---|---|
| Barley | 40 | 30 |
| Chenopodium | 90 | 80 |
| Emex | 90 | 90 |
| Raphanus | 80 | 70 |
| Setaria | 80 | 80 |

The same results are obtained by formulating a compound of formulae I and IIa to IIq in accordance with Examples F1, F2 and F4 to F7.

EXAMPLE B3

Post-emergent applications of mixtures of a herbicide of formula I with a safener of formulae IIa to IIq to durum wheat.

Under greenhouse conditions, durum wheat is grown in plastic pots to the 2.5-leaf stage. In this stage, both the herbicide of formula I alone and the mixture of the herbicide with a safener of formulae IIa to IIq are applied to the test plants. The test substances (Formulation Examples F3 a) and b)) are applied as aqueous suspension with 500 l water/ha. Ten days after the application, the results are evaluated on a percent scale. The results obtained show that, with the safeners of formulae IIa to IIq, the damage caused to durum wheat can be markedly reduced by the herbicide of formula I. Examples of the selective effect of the compositions of the invention are given in Table B12:

TABLE B12

| Plant: | Herbicide of formula 1:250 g/ha | Herbicide of formula 1:250 g/ha Safener no. 2,01: 60 g/ha |
|---|---|---|
| Durum wheat | 30 | 10 |
| Chenopodium | 90 | 95 |
| Emex | 90 | 90 |
| Raphanus | 90 | 80 |
| Setaria | 80 | 80 |

What is claimed is:

1. A selective herbicidal composition comprising, in addition to customary inert formulation assistants, a mixture of a) a herbicidally effective amount of a herbicide of formula I

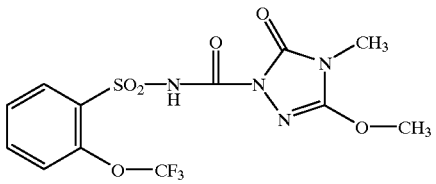

and b) to antagonise the herbicide, an antidotally effective amount of a safener of formula 1.02

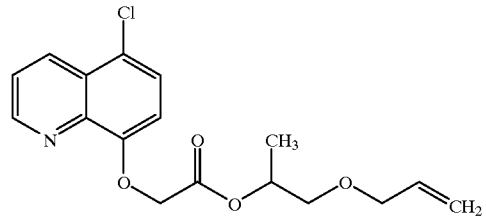

or of formula IIq

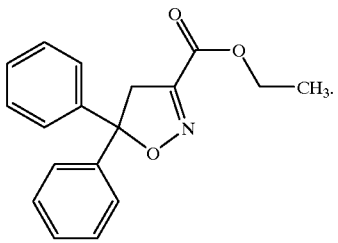

2. A method of selectively controlling weeds in crops of cultivated plants, which comprises treating said cultivated plants, the seeds or seedlings or the crop area thereof with a herbicidally effective amount of the compound of formula I

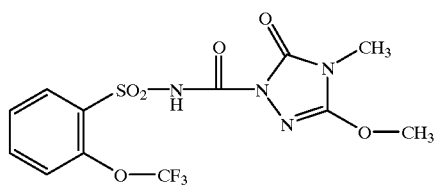
(I)

and b) to antagonise the herbicide, an antidotally effective amount of a safener of formula 1.02 or IIq

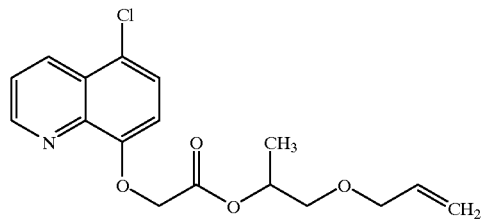
(1.02)

(IIq)

3. A method according to claim 2, which comprises treating crops of cultivated plants, or areas intended for cropping with cultivated plants, with 0.001 to 2 kg/ha of a herbicide of formula I and an amount of 0.001 to 0.5 kg/ha of a safener of formula 1.02 or IIq.

4. A method according to claim 2 wherein the cultivated plants are cereals or rice.

* * * * *